(12) United States Patent
Schweers et al.

(10) Patent No.: US 6,433,194 B1
(45) Date of Patent: Aug. 13, 2002

(54) SEPARATION OF TRIOXANE FROM LIQUID MIXTURES

(75) Inventors: Elke Schweers; Albert Reichl, both of Bad Soden; Stefan Heffels, Eppstein, all of (DE)

(73) Assignee: Ticona GmbH (DE)

( * ) Notice: Subject to any disclaimer, the term of this patent is extended or adjusted under 35 U.S.C. 154(b) by 0 days.

(21) Appl. No.: 09/787,263

(22) PCT Filed: Sep. 16, 1999

(86) PCT No.: PCT/EP99/06843

§ 371 (c)(1),
(2), (4) Date: May 24, 2001

(87) PCT Pub. No.: WO01/17188

PCT Pub. Date: Mar. 30, 2000

(30) Foreign Application Priority Data

Sep. 17, 1998 (DE) .......................................... 198 42 579

(51) Int. Cl.⁷ ............................................ C07D 323/06

(52) U.S. Cl. .......................................... 549/368; 203/14

(58) Field of Search .............................. 549/368; 203/14

(56) References Cited

U.S. PATENT DOCUMENTS

| | | | | | |
|---|---|---|---|---|---|
| 2,347,447 | A | * | 7/1944 | Walker et al. ............... | 549/368 |
| 4,043,873 | A | * | 8/1977 | Ackermann et al. ........ | 549/368 |
| 5,061,349 | A | * | 10/1991 | Kupenbender et al. ..... | 549/368 |
| 5,401,859 | A | * | 3/1995 | Muck et al. ................ | 549/368 |
| 6,121,467 | A | * | 9/2000 | Kniep et al. ................ | 549/368 |
| 6,201,136 | B1 | * | 3/2001 | Reichl et al. ............... | 549/368 |

* cited by examiner

*Primary Examiner*—Alan L. Rotman
*Assistant Examiner*—Raymond Covington
(74) *Attorney, Agent, or Firm*—Connolly Bove Lodge & Hutz LLP

(57) ABSTRACT

Process for the removal of trioxane from a liquid mixture comprising trioxane, formaldehyde, alcohol, hemiformals formed from the form-aldehyde and the alcohol, usual secondary components arising in the preparation of trioxane, and, in addition or as an alternative to the alcohol and the hemiformals, water, in which the trioxane is transferred into the gas phase by vaporization or evaporation and subsequently converted into a liquid state by condensation and obtained as condensate or converted into a solid state by desublimation and obtained as desublimate. Through the process, an increase in the concentration of the trioxane by 2.5 times or more is achieved.

9 Claims, 1 Drawing Sheet

Figur 1:
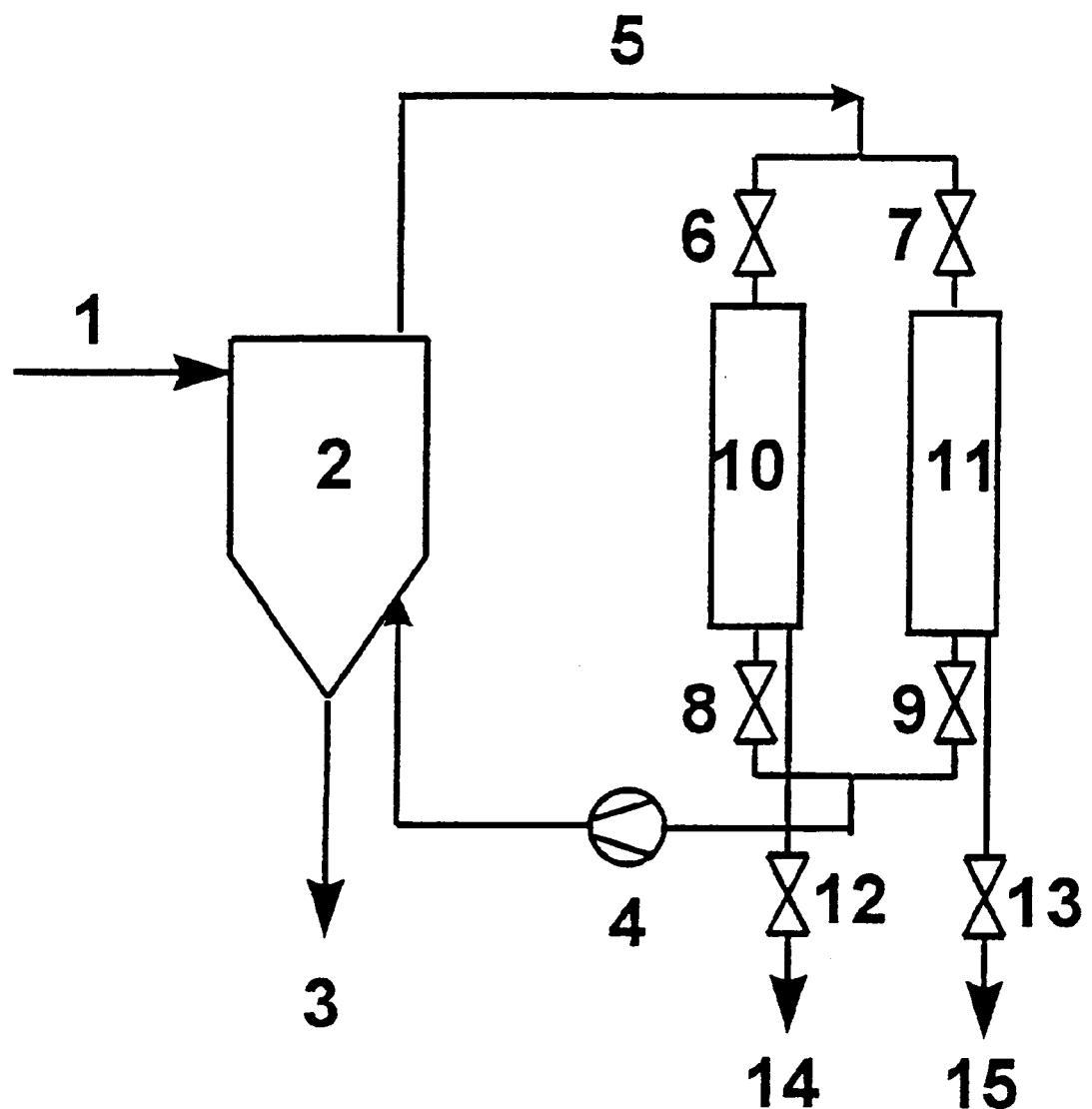

SEPARATION OF TRIOXANE FROM LIQUID MIXTURES

The invention relates to the removal of trioxane from a liquid mixture comprising trioxane, formaldehyde, alcohol, hemiformals formed from formaldehyde and alcohol, and small amounts of secondary components. In addition or as an alternative to the alcohol and the hemiformals, the mixture may also comprise water and reaction products formed from formaldehyde and water.

For the preparation of the engineering plastic polyacetal, in particular of polyoxymethylene (POM), high-purity trioxane is required. The quality of the plastic, i.e. the achievable degree of polymerization, is, besides the polymerization conditions, determined principally by the purity of the trioxane.

Various processes for the preparation of trioxane are known (for example homogeneously or heterogeneously catalyzed from aqueous formaldehyde solutions (AT 252913) or heterogeneously catalyzed from gaseous formaldehyde on heteropolyacids (EP 0606056). Irrespective of the preparation process, trioxane is generally not produced as a pure substance, but instead always as a mixture with unreacted formaldehyde and other substances, such as alcohol, water and small amounts of other components, so-called secondary components, such as methanol, methyl formate, methylal, formic acid, dioxolane and tetraoxane. For use of the trioxane in the polymerization, this must be separated, in particular from the formaldehyde, and may only contain small amounts of secondary components.

A multiplicity of literature is known relating to the removal of trioxane from aqueous formaldehyde-containing mixtures. The separation of gaseous mixtures of formaldehyde and trioxane is only described in a few places.

The separation from aqueous solution has hitherto been carried out, in particular, by distillation (AT 252913 and JP 83/171278). In the distillation, unreacted formaldehyde is frequently fed back into the reactor, where it is reacted further to give trioxane. A limit for the increase in the concentration of trioxane by distillative removal arises through an azeotrope of trioxane with water which boils at 92° C. and 1 bar and which generally has a trioxane content of about 70% by weight. A further disadvantage of this process is possible solids formation by polymerization of formaldehyde or formation of paraformaldehyde, especially in the region of the column head. In order to avoid same, all apparatus parts must either be heated to temperatures above 100° C. (for example at a formaldehyde partial pressure of 1 bar) or wetted with a liquid.

A further process for the separation of formaldehyde and trioxane from aqueous solutions comprises the extraction of the trioxane with organic solvents in which trioxane has higher physical solubility than formaldehyde. This process has exclusively been employed for the removal of trioxane from the aqueous phase. Examples of organic extractants used are saturated aliphatic or aromatic hydrocarbons or halogenated hydrocarbons (EP 0583907) which are sparingly miscible or even immiscible with water. A disadvantage of the extraction is that an additional substance in the form of the organic solvent is introduced into the process, which makes subsequent work-up of the organic phase necessary too. A further disadvantage is that large parts of the trioxane sometimes also remain in the aqueous phase. Large amounts of trioxane therefore have to be circulated or are lost in the work-up process.

A further possibility described for the selective removal from an aqueous formaldehyde/trioxane phase is crystallization of the trioxane (DE 3508668). The trioxane concentration in the aqueous mixture must be greater than 50% by weight here.

In the preparation of trioxane by trimerization of formaldehyde from aqueous formalin solutions, the above-mentioned processes of azeotropic distillation, extraction and, if desired, crystallization are generally linked with one another in a suitable manner in order to obtain trioxane in the requisite high purity.

For the separation of gaseous mixtures of formaldehyde and trioxane, selective absorption of one species has frequently been employed. In general, either the formaldehyde is chemisorbed and the trioxane left in the gas phase (GB 1245990) or conversely selective physisorption of the trioxane is carried out (EP 0680959). Since no liquid phase in which either only the formaldehyde or only the trioxane is soluble has been found, fractions of the respective other species are also bound here. For this reason, the purities necessary for polymerization cannot be achieved using this process. Furthermore, large losses of the valuable product trioxane occur.

The separation of a mixture of formaldehyde and trioxane in gaseous form with a low water content by absorption of the trioxane in an alcohol followed by crystallization from the alcoholic solution is described in the as yet unpublished German Patent Application No. 19833620.9. This process forms a possible step in a novel process for the preparation of trioxane from methanol, consisting of the steps of non-oxidative dehydrogenation (DE 3920811), removal of formaldehyde (as yet unpublished German Patent Application Nos. 19747647.3 and 19748380.1), formaldehyde trimerization (EP 0606056 and EP 0691388) and removal of trioxane (for example in accordance with German Patent Application No. 19833620.9).

The object was to find an alternative process for the removal of trioxane from a liquid mixture comprising trioxane, formaldehyde, alcohol, hemiformals formed from formaldehyde and the alcohol, secondary components and, in addition or as an alternative to the alcohol and the hemiformals, water and reaction products formed from formaldehyde and water, in which the aim was to obtain the trioxane in high purity. The other valuable products present in the mixture, namely formaldehyde and possibly the alcohol, should if possible be present in other product streams that can be utilized.

This object is achieved in accordance with the invention by transferring trioxane as selectively as possible from the liquid mixture into the vapor phase in a suitable manner, and subsequently removing it selectively in liquid or solid form by cooling and subsequent condensation or desublimation.

The invention therefore relates to a process for the recovery of trioxane in which the trioxane is transferred from a liquid mixture comprising trioxane, formaldehyde, alcohol, hemiformals formed from the formaldehyde and the alcohol, usual small amounts, formed in the preparation of trioxane, of lower- and higher-boiling secondary components and, in addition or as an alternative to the alcohol and the hemiformals, water, into the gas phase by volatilization or evaporation and subsequently converted into a liquid state by condensation and isolated as condensate or converted into a solid state by desublimation and isolated as desublimate.

The invention also relates to the use of the trioxane condensate or desublimate obtained by the process according to the invention, which is characterized by its composition and a trioxane content of at least 80% by weight, for the preparation of polymers and fuels or for obtaining formaldehyde by depolymerization.

Examples of usual secondary components are methanol, methyl formate, tetraoxane, dioxolane, trioxy ether and traces of formic acid. The alcohol present in the liquid starting mixture, which in some cases is able to form hemiformals with the formaldehyde, is preferably a monohydric alcohol, for example cyclohexanol, methanol, propanol or butanol. However, it is also possible to use other alcohols, including polyhydric ones, such as glycerol, diethylene glycol, triethylene glycol, triethanolamine, butanetriol and pentanetriol. If desired, it is also possible to use a mixture of alcohols. The alcohol should preferably have a higher boiling point and a lower melting point than trioxane.

In contrast to German Patent Application No. 19833620.9 and DE 3508668, the process according to the invention achieves, in particular, the object of separating the mixture in liquid form with a low water content, as arises, for example, in the absorption step after the process according to German Patent Application No. 19833620.9 and thus in the above-mentioned novel process for the preparation of trioxane from methanol. However, the process can also be used for mixtures having a higher water content.

Surprisingly, it has been found that the process according to the invention enables a high concentration of trioxane to be achieved even for a very low initial concentration of the trioxane in the liquid mixture.

In order to isolate the trioxane by the process according to the invention, the trioxane is firstly transferred from the liquid mixture into the vapor phase at a temperature in the range from 20 to 200° C., preferably in the range from 50 to 100° C., in a suitable apparatus with or without carrier gas. The trioxane is subsequently converted from the vapor phase into a liquid or solid physical state, i.e. condensed or desublimed, at a temperature in the range from −20 to 113° C., preferably in the range from 20 to 40° C. The process can be carried out at reduced pressure, atmospheric pressure or superatmospheric pressure, application of atmospheric pressure being preferred.

In contrast to DE 3508668, the removal in the process according to the invention is preferably carried out from a low-water liquid mixture. Low-water here means that the mixture either contains no water at all, i.e. 0% by weight, or alternatively contains a maximum of 5% by weight, preferably a maximum of 3% by weight of water. This is a particular advantage compared with the prior art, since the low water content means that significantly less heating energy is necessary in the process and there is virtually no need to work up aqueous mixtures. The restriction present in the process according to DE 3508668 to mixtures having a trioxane content of greater than 50% is also absent in the process according to the invention. In addition, however, the process according to the invention can also be employed for the purification of trioxane from aqueous mixtures which have a significantly greater water content than 5%.

In contrast to the process for the removal of trioxane by crystallization in a liquid solution, either on cooled walls or in suspension, which is described in German Patent Application No. 19833620.9, the trioxane in the process according to the invention is firstly selectively vaporized or evaporated and subsequently converted into a liquid state (condensate) or—preferably—into a solid state (desublimate) by condensation or desublimation. Higher purities and yields can thereby be achieved than in the process according to German Patent Application No. 19833620.9.

Furthermore, the process according to the invention is more advantageous from the energetic point of view and thus with respect to the operating costs, since in the crystallization in accordance with German Patent Application No. 19833620.9, cold is used, which is not necessary in the process according to the invention. The apparatus costs to be expected are also lower in the process according to the invention than in the layer crystallization described in German Patent Application No. 19833620.9.

For the transfer of a trioxane from the liquid mixture into the vapor phase, it is advantageous in the process according to the invention, but not absolutely necessary, for trioxane (boiling point at atmospheric pressure 113° C.) to have a comparatively high vapor pressure compared with the other components. If the cooling is carried out as a desublimation, the comparatively high melting point (about 62° C.) of trioxane proves to be particularly advantageous. The selective removal of trioxane from the vapor phase that this makes possible means that the vapor phase can also contain lower- and higher-boiling components.

A number of possibilities exists for transferring the trioxane from the liquid phase into the vapor phase in the process according to the invention. Thus, for example, if the trioxane content in the mixture is sufficiently high, simple evaporation at atmospheric pressure can be carried out by increasing the temperature. A disadvantage here is the relatively high thermal load, which can result in liberation of formaldehyde from the hemiformal.

The transfer of trioxane into the vapor phase can also take place by atomization or evaporation under reduced pressure. Advantageous here are the low temperatures, but possible leak problems and the requisite complexity for the provision of the vacuum are disadvantageous.

The use of a carrier gas, which may also be preloaded with trioxane, proves particularly advantageous in the process according to the invention. This carrier gas is used to strip trioxane out of the liquid mixture. Both the advantageously lower temperatures and operation under atmospheric pressure are achieved in this case. In order to avoid an excessive demand for gas, however, use should be made of a compressor, by means of which the carrier gas is circulated between the vaporization or evaporation step and the condensation or desublimation step. Examples of suitable carrier gases are inert gases, such as nitrogen and argon.

If the atomization or evaporation step in the process according to the invention is carried out in a thermally gentle manner under moderate temperatures, it proves particularly advantageous that virtually no release of formaldehyde from the hemiformal occurs. This avoids problems with coating formation, for example due to precipitation of paraformaldehyde from the gas phase.

A number of apparatuses can be employed for the transfer of trioxane into the vapor phase in the process according to the invention. Thus, this process step can be carried out, for example, in evaporators, such as falling-film or thin-film evaporators. However, externally heated columns are also conceivable, which can be designed as spray towers and optionally have internals, such as trays or structured packing. It is also possible to use a heated stirred vessel or alternatively a bubble-tray column, in particular if a carrier gas is used. Also conceivable is the use of flash apparatuses, in which superheated solutions are decompressed to a lower pressure.

Preference is given to apparatuses which, as standard apparatuses with a simple design and continuous operation, have a sufficiently large vapor/liquid phase interface and high throughputs. These requirements are satisfied, for example, by evaporators, such as falling-film or thin-film evaporators.

The vaporization or evaporation can be carried out in the process according to the invention at temperatures in the range from 20 to 200° C., also at lower temperatures, if desired, in the reduced-pressure range and also at higher temperatures, if desired, in the superatmospheric pressure range, but preferably at a temperature of from 50 to 100° C. The liquid stream flowing out of the vaporization or evaporation step, which is depleted in trioxane, but comprises the valuable products formaldehyde, alcohol and hemiformals, can be fed back into an earlier step of the overall process described above or used elsewhere, for example for recovery of the valuable products present therein. It is furthermore conceivable to feed some or all of the stream back into the vaporization or evaporation step. In the latter case, a batchwise operating procedure is preferably present.

Through the condensation or desublimation of the trioxane from the vapor phase, the trioxane can be obtained in the process according to the invention either in the liquid state or in the solid state. If the condensate is to remain liquid, relatively high temperatures must be set in the condensation step in view of the melting point of trioxane, but this causes the heat and thus mass transfer and the deposition rate to be minimized. Condensers which can be employed here are all known types of heat exchanger with vapor-liquid phase transition; mention may be made here merely by way of example of tube-bundle heat exchangers.

The trioxane can also be condensed or absorbed out of the gas phase charged therewith by contact with a cold liquid. Likewise suitable for this purpose are, for example, falling-film condensers, bubble-tray columns or stirred vessels operated with corresponding cold liquids or solvents. However, a disadvantage in this set-up is the purification which is subsequently necessary, i.e. the removal of the trioxane from the liquid.

The condensation as far as the liquid phase can be carried out in the process according to the invention at temperatures in the range from 30 to 113° C., in the case of condensation under excess pressure if desired also at higher temperatures, but preferably at temperatures in the range from 30 to 75° C.

However, it is advantageous to use desublimation in the process according to the invention with utilization of the high melting point of trioxane. This can be carried out here both on rigid, cooled walls and in a moved zone, for example in a fluid bed or a fluidized bed. A further advantage of desublimation is that, by varying the process parameters, specific shaping of the trioxane desublimate can be carried out, for example deposition in a desired particle size. The desublimation process can be supported in the process according to the invention by suitable measures, such as admixing a cold gas or injecting a low-boiling solvent.

If rigid walls are employed for the desublimation, the sublimate can be removed from them either by melting or by mechanical cleaning, such as scraping-off. Mechanical cleaning is more advantageous here if the product must then be processed further in liquid form, since no additional energy, as required, for example, for melting, has to be supplied, and because the process can be operated continuously. The apparatus employed can be, for example, a scraped-shell condenser. Owing to the relatively low heat-transfer coefficient in the vapor-solid phase transition, large exchange surfaces are generally necessary. From this point of view, the use of plate or finned tube heat exchangers is particularly advantageous, from which the solid coating can be removed by melting or by sublimation, preferably supported by a temperature increase and a pressure reduction. Instead of plate or finned tube heat exchangers, it is also possible to employ other types of heat exchanger, for example tube-bundle heat exchangers. Operation is generally in cycles, i.e. at least two heat exchangers are used in a continuous process.

If the desublimation is carried out in a fluid bed or a fluidized bed, higher heat exchange coefficients can be achieved in continuous operation. Fluid bed desublimation can be carried out with or without addition of a flow agent, preferably also with addition of a cooled gas. Examples of apparatuses which can be employed are fluidized-bed dryers; filtrations or sieving of the particles can, if desired, be carried out downstream.

The desublimation can be carried out in the process according to the invention at temperatures in the range from −20 to 70° C., under certain circumstances also at lower temperatures, but preferably at temperatures in the range from 20 to 40° C., since generation of low temperatures is unnecessary for this purpose, which represents a major advantage of the process according to the invention. If melting is necessary, this can be carried out at temperatures in the range from 30 to 113° C., also at higher temperatures in the superatmospheric pressure range, but preferably at temperatures in the range from 60 to 80° C.

One possibility for carrying out the process steps of vaporization or evaporation and condensation and desublimation in a single apparatus arises on use of a short-path evaporator, in which the evaporation and condensation surfaces are arranged concentrically. The short-path evaporator allows particularly gentle handling of the product. If the condensation surface is employed as desublimator, cycled operation is necessary. The short-path evaporator can also be designed as a molecular condenser or desublimator.

If the trioxane removed from the liquid mixture by a vaporization or evaporation step and condensation or desublimation step does not yet have the desired purity, multistep operation with corresponding recycling can be implemented in the process according to the invention. It is furthermore conceivable for the product present after one step to be subjected to fine purification with the aid of other separation methods.

The trioxane obtained by the process according to the invention generally comprises from 2 to 4% by weight of formaldehyde, from 4 to 8% by weight of alcohol and more than 80% by weight, preferably from 85 to 90% by weight, of trioxane. It is suitable for all areas of application, such as polymerization to give plastics, such as polyacetals, in particular polyoxy-methylene, the preparation of fuels and the depolymerization to give formaldehyde, which facilitates further use for all known formaldehyde reactions, in particular if very pure formaldehyde is necessary for this purpose.

Overall, a trioxane condensate or desublimate whose trioxane content corresponds to 2.5 times or more the trioxane content in the liquid starting mixture can be obtained using the process according to the invention. However, if the trioxane content in the liquid mixture is extremely low, for example only 5% by weight, although it is not possible to obtain a trioxane content of 80% by weight or more in the condensate or desublimate, it is nevertheless possible to achieve an enrichment of the trioxane by tenfold, i.e. to about 50 to 65% by weight.

The process according to the invention is distinguished over the processes employed hitherto by the following advantages:

high purities and yields of trioxane,
in the case of aqueous mixtures, no restriction by the water/trioxane azeotrope, in contrast to distillation,
simple apparatus implementation using standard units possible,
low formaldehyde contents, even after one process step, and thus favorable prerequisites for further processing, very low formaldehyde concentrations in the gas phase and thus prevention of solid or coating formation (for example paraformaldehyde), due to moderate temperatures, thermally gentle and energetically advantageous in the vaporization or evaporation step; consequently prevention of the release of gaseous formaldehyde, energetically advantageous in the condensation or desublimation step due to the possibility of using river water, recooling water or ambient air for cooling, avoiding comparatively expensive generation of cold, in addition energetically advantageous due to internal energy recovery, high operational reliability, no need for any auxiliary materials, which have to be separated off in a complex manner, no loss streams: discharge from the vaporizer or evaporator step can be employed elsewhere in the process, no formation of a preliminary fraction from a sweating process in the condensation or desublimation step.

A possible apparatus implementation of the process according to the invention is explained below with reference to FIG. 1.

The liquid starting mixture 1, which, besides trioxane, also comprises formaldehyde, an alcohol (preferably having a higher boiling point than trioxane, such as, for example, cyclohexanol), hemiformals and secondary components, and in addition or as an alternative to alcohol and hemiformal, also water, is fed to the apparatus for transfer of the trioxane into the vapor phase, the apparatus being designed here as the evaporator 2. The liquid flows through the evaporator 2 from top to bottom and exits again at the bottom as stream 3, which is depleted in trioxane. The compressor 4 conveys a circulation stream 5 of inert carrier gas (for example nitrogen or argon) through the evaporator in countercurrent to the liquid, the carrier-gas stream being loaded with trioxane. The loaded carrier-gas stream is passed to one of the heat exchangers 10 and 11, which are designed here as desublimers, through a corresponding position of the stop cocks 6 and 7 and the corresponding position of the stop cocks 8 and 9. Under the prerequisite of a sufficiently large temperature difference between the evaporator 2 and the heat exchanger 10 or 11, trioxane precipitates in solid form in the first heat exchanger charged with gas. If this first heat exchanger is loaded, the gas stream is passed to the other heat exchanger via the stop cocks 6 to 9. The desublimate is melted in the loaded heat exchanger by an increase in temperature and can be taken off via the stop cocks 12 or 13 as stream 14 or 15. If the second heat exchanger is loaded, the gas stream is fed back to the previously emptied heat exchanger, and the desublimate is melted and taken off in the now loaded heat exchanger.

The apparatus circuit according to FIG. 1 represents only one conceivable variant of the process according to the invention. As described above, other physical principles and apparatuses for the removal of the trioxane by transfer from the liquid phase into the vapor phase and back to the liquid or solid phase can also be employed in the process according to the invention.

The fact that only moderate temperatures are necessary in the process according to the invention enables heat arising in other process steps to be utilized here in an advantageous manner. If, for example, as described above, the process according to the invention is combined with prior trimerization of formaldehyde from the gas phase, the heat liberated during the trimerization can be employed for heating the vaporizer or evaporator. If the heating medium leaving the vaporizer or evaporator is at a sufficiently high temperature level, it can be fed on to the desublimers for the purpose of melting the product. In this way, the thermal energy employed in the process as a whole can be utilized in an optimum manner.

The process according to the invention is illustrated below with reference to some experimental studies. The experimental set-up was carried out in accordance with the apparatus variants shown in FIG. 1.

In all experiments, the evaporator 2 used was a thin-film evaporator DN25 with a double-jacket evaporator body made of glass; the desublimers 10 and 11 used were double-jacket tubes DN50 made of glass.

The feed 1,400 ml/h in all experiments, consisted of a liquid mixture comprising trioxane, cyclohexanol, formaldehyde and secondary components (principally methanol and water), in which the formaldehyde was predominantly in bound form as cyclohexyl hemiformal (results, see Table 1). For comparison, a feed comprising water instead of cyclohexanol was also investigated (results, see Table 2).

The carrier gas used was nitrogen. All experiments were carried out at atmospheric pressure or a slight excess pressure in the nitrogen circuit. Samples were taken from the entering and exiting liquid streams and analyzed using a gas chromatograph. All percentages in this respect are taken to mean percent by weight.

In Tables 1 and 2, the following abbreviations are furthermore used:

FA formaldehyde TOX trioxane
MeOH methanol CHOL cyclohexanol
H2O water

TABLE 1

Experimental parameters and results in the experiments with low-water feed

| Experiment | Temp. jacket evaporator ° C. | Temp. jacket desublimer ° C. | Carrier gas N₂ l/h | Feed FA % | Feed TOX % | Feed CHOL % | Cycle time h | Desublimate Flow rate g/h | Desublimate FA % | Desublimate TOX % | Desublimate CHOL % |
|---|---|---|---|---|---|---|---|---|---|---|---|
| Desu 3A | 60 | 2  | 300 | 16.2 | 31.5 | 50.4 | 0.5 | 53  | 2.5 | 87.3 | 5.1 |
| Desu 3B | 80 | 25 | 300 | 16.3 | 30.9 | 50.7 | 0.5 | 103 | 3.1 | 85.9 | 7.5 |
| Desu 3C | 60 | 2  | 300 | 23.4 | 30.9 | 43.5 | 0.5 | 52  | 2.6 | 88.3 | 4.0 |
| Desu 3D | 80 | 25 | 300 | 23.5 | 30.7 | 43.5 | 1   | 98  | 3.4 | 87.4 | 5.7 |
| Desu 3E | 80 | 2  | 300 | 24.2 | 29.0 | 44.6 | 0.3 | 63  | 3.0 | 87.7 | 4.3 |
| Desu 4A | 80 | 25 | 300 | 21.5 | 30.8 | 45.9 | 0.5 | 101 | 3.3 | 88.0 | 6.3 |

TABLE 1-continued

Experimental parameters and results in the experiments with low-water feed

| Experiment | Temp. jacket evaporator °C. | Temp. jacket desublimer °C. | Carrier gas N₂ l/h | Feed FA % | Feed TOX % | Feed CHOL % | Cycle time h | Flow rate g/h | Desublimate FA % | Desublimate TOX % | Desublimate CHOL % |
|---|---|---|---|---|---|---|---|---|---|---|---|
| Desu 4B | 80 | 25 | 450 | 21.5 | 30.8 | 45.9 | 0.5 | 115 | 3.0 | 87.5 | 7.4 |
| Desu 4C | 80 | 25 | 200 | 21.5 | 30.8 | 45.9 | 0.5 | 84 | 3.4 | 88.4 | 5.6 |
| Desu 4D | 80 | 25 | 300 | 18.8 | 31.2 | 48.2 | 0.5 | 99 | 2.6 | 88.4 | 6.9 |
| Desu 4E | 80 | 25 | 300 | 18.9 | 30.9 | 48.3 | 1.5 | 103 | 2.8 | 88.0 | 7.3 |
| Desu 5A | 80 | 25 | 300 | 17.6 | 39.9 | 39.6 | 0.5 | 118 | 3.0 | 87.7 | 5.8 |
| Desu 5B | 75 | 25 | 450 | 19.5 | 31.8 | 47.0 | 0.5 | 95 | 2.4 | 88.9 | 7.0 |
| Desu 5C | 75 | 25 | 450 | 19.5 | 31.8 | 47.0 | 1.5 | 96 | 2.7 | 88.1 | 7.5 |
| 980707A | 75 | 25 | 300 | 15.5 | 28.9 | 54.6 | 1 | 83 | 2.8 | 85.5 | 8.6 |
| 980707B | 75 | 25 | 300 | 15.5 | 28.9 | 54.6 | 0.25 | 80 | 2.8 | 84.6 | 9.7 |
| 980707C | 85 | 25 | 200 | 15.5 | 28.9 | 54.6 | 0.5 | 100 | 3.5 | 83.1 | 9.6 |
| 980707D | 85 | 25 | 400 | 15.5 | 28.9 | 54.6 | 0.5 | 125 | 3.5 | 78.4 | 14.7 |
| 980708A | 85 | 25 | 300 | 14.6 | 29.0 | 54.2 | 0.5 | 111 | 3.2 | 82.6 | 11.0 |
| 980708B | 85 | 25 | 350 | 14.6 | 29.0 | 54.2 | 0.5 | 120 | 3.3 | 81.3 | 12.4 |
| 980805A | 70 | 5 | 300 | 24.9 | 5.3 | 66.6 | 1 | 21.3 | 10.7 | 64.6 | 11.2 |
| 980805B | 60 | 5 | 300 | 20.1 | 3.9 | 73.5 | 2 | 16.4 | 12.1 | 51.7 | 21.0 |
| 980805C | 60 | 5 | 300 | 21.5 | 4.4 | 71.5 | 2.17 | 19.3 | 12.2 | 53.7 | 21.0 |
| 980805C | 60 | 5 | 300 | 23.1 | 3.2 | 71.6 | 5 | 15.3 | 12.0 | 55.6 | 20.2 |
| 980805C | 60 | 5 | 300 | 23.6 | 3.3 | 71.1 | 2.33 | 12.9 | 12.7 | 51.7 | 22.3 |

TABLE 2

Experimental parameters and results in the experiments with water-containing feed

| Experiment | Temp. jacket evaporator °C. | Temp. jacket desublimer °C. | Carrier gas N₂ l/h | Feed FA % | Feed H2O % | Feed MeOH % | Feed TOX % | Cycle time h | Flow rate g/h | Desublimate FA % | Desublimate H2O % | Desublimate MeOH % | Desublimate TOX % |
|---|---|---|---|---|---|---|---|---|---|---|---|---|---|
| 980714A | 70 | 20 | 300 | 10.1 | 13.3 | 4.2 | 72.4 | 0.5 | 154 | 2.3 | 18.2 | 2.6 | 76.9 |
| 980714B | 60 | 20 | 300 | 10.1 | 13.3 | 4.2 | 72.4 | 0.5 | 90 | 2.2 | 17.5 | 2.5 | 77.8 |

In all experiments, the trioxane was obtained as needle-shaped desublimate; the needles formed a braid and in some cases bridges over the cross section of the desublimers. These did not hinder the flow of the circulated carrier-gas stream. Instead, the braid advantageously prevented discharge of solid particles from the desublimer with the gas stream, which rendered superfluous the use of a downstream filter or separator, as is entirely conventional in other desublimers.

In the examples described above regarding the process according to the invention, surprisingly high purities and yields were obtained in spite of the simple, one-step set-up. Thus, it was possible to concentrate trioxane from low-water solution from about 30% by weight to about 90% by weight, with yields of about 80% being achieved. The formaldehyde is greatly depleted in the desublimate compared with the feed, which is advantageous for further processing of the desublimate. The discharge from the evaporator is highly depleted in trioxane. Thus, for example, only 9.0% of TOX with 28.4% of FA and 61.0% of CHOL are found in the discharge in Experiment DESU4B; the discharge in Experiment 980708A contains only 6.7% of TOX with 19.7% FA and 72.2% of CHOL.

A further surprising fact in the experiments was that no preliminary fraction, i.e. no condensate from a sweating process, had to be taken off during melting of the desublimate, but instead the entire contents of the desublimer were usable as product. This results in an advantageous increase in the throughput with a reduction in the cycle times. If, by contrast, a preliminary fraction is taken off during melting, the purity of the product can advantageously even be increased in the process according to the invention.

Instead of the apparatuses used in the examples mentioned, all other apparatuses described above are also conceivable for the experiment. Thus, for example, a falling-film evaporator can be employed instead of the thin-film evaporator. The desublimation can also be carried out, for example, using thinned tube heat exchangers or using fluid-bed apparatuses.

List of Reference Symbols

1 Feed line for the liquid starting mixture
2 Evaporator
3 Take-off of the trioxane-depleted liquid after the evaporator
4 Compressor for carrier gas (circulation gas)
5 Carrier-gas stream (circulation gas)
6 Stop cock
7 Stop cock
8 Stop cock
9 Stop cock
10 Heat exchanger (desublimer)
11 Heat exchanger (desublimer)

12 Stop cock
13 Stop cock
14 Take-off of the product from the heat exchanger (desublimer)
15 Take-off of the product from the heat exchanger (desublimer)

What is claimed is:

1. A process for the recovery of trioxane, in which the trioxane is transferred from a liquid mixture comprising trioxane, formaldehyde, alcohol, hemiformals formed from the formaldehyde and the alcohol, usual secondary components arising in the preparation of trioxane, and, in addition or as an alternative to the alcohol and the hemiformals, water and reaction products formed from formaldehyde and water, into the gas phase by volatilization or evaporation and subsequently converted into a liquid state by condensation and isolated as condensate or converted into a solid state by desublimation and isolated as desublimate, and wherein the condensate or the desublimate has a trioxane content which is at least 2.5 times as high as the trioxane content in the liquid mixture, and wherein the process is carried out using a carrier gas.

2. The process as claimed in claim 1, wherein the liquid mixture essentially comprises trioxane, formaldehyde, alcohol, hemiformals formed from the formaldehyde and the alcohol, usual secondary components arising in the preparation of trioxane, and from 0 to 5% by weight, preferably from 0 to 3% by weight, of water.

3. The process as claimed in claim 1, wherein the condensate or the desublimate has a trioxane content of at least 80% by weight.

4. The process as claimed in claim 1, wherein the vaporization or evaporation is carried out at a temperature in the range from 20 to 200° C., the vaporization or evaporation optionally being carried out at reduced pressure, superatmospheric pressure or atmospheric pressure.

5. The process as claimed in claim 4, wherein the vaporization or evaporation is carried out at a temperature in the range from 50 to 100° C.

6. The process as claimed in claim 1, wherein a condensation is carried out at a temperature in the range from 30 to 113° C., preferably at a temperature in the range from 30 to 75° C., or a desublimation is carried out at a temperature in the range from −20 to 70° C., preferably at a temperature in the range from 20 to 40° C.

7. The process as claimed in claim 1, wherein the vaporization or evaporation and the condensation or desublimation is optionally each carried out in a one-step or multistep process.

8. The process as claimed in one of claims 1, 2 or 3–6 wherein the vaporization or evaporation is carried out in at least one apparatus selected from evaporators, columns, stirred vessels, bubble-tray columns and flash apparatuses, and the condensation or desublimation is carried out in at least one apparatus selected from heat exchangers, fluid-bed apparatuses, fluidized-bed apparatuses, bubble-tray columns and stirred vessels.

9. The process of claim 1 wherein the water content is 0 to 5% by weight.

* * * * *